(12) United States Patent
Renaud

(10) Patent No.: US 11,389,331 B2
(45) Date of Patent: *Jul. 19, 2022

(54) EYE MASK

(71) Applicant: Nicole Kyongnan Renaud, Arlington, VA (US)

(72) Inventor: Nicole Kyongnan Renaud, Arlington, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/887,349

(22) Filed: May 29, 2020

(65) Prior Publication Data

US 2020/0289322 A1    Sep. 17, 2020

Related U.S. Application Data

(63) Continuation of application No. 15/689,587, filed on Aug. 29, 2017, now Pat. No. 10,667,951.

(60) Provisional application No. 62/380,534, filed on Aug. 29, 2016.

(51) Int. Cl.
*A61F 9/04* (2006.01)
*A61F 7/00* (2006.01)
*A61F 7/02* (2006.01)

(52) U.S. Cl.
CPC ............... *A61F 9/04* (2013.01); *A61F 7/007* (2013.01); *A61F 7/02* (2013.01); *A61F 2007/0004* (2013.01); *A61F 2007/0071* (2013.01); *A61F 2007/0078* (2013.01); *A61F 2007/0086* (2013.01); *A61F 2007/0094* (2013.01); *A61F 2007/023* (2013.01)

(58) Field of Classification Search
CPC .......................... A61F 2007/0004; A61F 9/04
See application file for complete search history.

(56) References Cited

U.S. PATENT DOCUMENTS

| | | |
|---|---|---|
| 3,173,419 A | 3/1965 | Dubilier et al. |
| 5,169,384 A | 12/1992 | Bosniak et al. |
| 5,720,773 A | 2/1998 | Lopez-Claros |
| 6,155,995 A | 12/2000 | Lin |
| 6,409,746 B1 | 6/2002 | Igaki et al. |
| 6,455,583 B1 | 9/2002 | Pflugfelder |
| 6,908,195 B2 | 6/2005 | Fuller |
| 6,974,470 B2 | 12/2005 | Tsunakawa et al. |
| 7,707,655 B2 | 5/2010 | Braunecker et al. |
| 7,976,573 B2 | 7/2011 | Korb |
| 8,636,786 B2 | 1/2014 | Biser |
| 9,421,124 B2 | 8/2016 | Carey et al. |
| 10,667,951 B2 * | 6/2020 | Renaud ............... A61F 7/007 |

(Continued)

OTHER PUBLICATIONS

Grinigh Long-lasting Herbal Lavender Steam Eye Mask, web page www.amazon.com, available at least by Aug. 28, 2016.

(Continued)

*Primary Examiner* — Kaitlyn E Smith
(74) *Attorney, Agent, or Firm* — Grasso PLLC

(57) ABSTRACT

Eye masks and associated processes are disclosed herein. These masks and associated processes may involve positioning a mask over the eyes and nearby glands of a user and applying heat and/or moisture. This treatment may provide therapeutic benefits, including therapy of Meibomian gland disease and other sources of dry eye. Other physical benefits can also include mechanically gently holding eyelids closed and promoting relaxation and reduction of stress.

23 Claims, 6 Drawing Sheets

(56) References Cited

U.S. PATENT DOCUMENTS

| | | |
|---|---|---|
| 2003/0014096 A1 | 1/2003 | Burkhart |
| 2004/0231671 A1 | 11/2004 | Begum |
| 2006/0058840 A1 | 3/2006 | Payne |
| 2007/0049913 A1 | 3/2007 | Grenon |
| 2007/0060988 A1 | 3/2007 | Grenon et al. |
| 2008/0109053 A1 | 5/2008 | Grenon et al. |
| 2010/0010598 A1 | 1/2010 | Igaki et al. |
| 2010/0241200 A1* | 9/2010 | Bruder ............... A61F 7/02 607/112 |
| 2011/0178585 A1 | 7/2011 | Biser |
| 2013/0013028 A1 | 1/2013 | Kriksunov et al. |
| 2014/0288624 A1 | 9/2014 | Wasko et al. |
| 2015/0012073 A1 | 1/2015 | Devine |
| 2015/0012074 A1 | 1/2015 | Devine |
| 2016/0220414 A1 | 8/2016 | Devine |
| 2016/0354250 A1 | 12/2016 | Paulson |
| 2017/0014300 A1 | 1/2017 | Dippo et al. |
| 2019/0060158 A1 | 2/2019 | Grenon et al. |
| 2019/0125579 A1 | 5/2019 | Habib |
| 2019/0142677 A1 | 5/2019 | Linder et al. |

OTHER PUBLICATIONS

Dry Eye Compress, Lifestance Eye Mask USB, web page www.amazon.com, available at least by Aug. 28, 2016.
Dry Eye Compress with HydroHeat Machine Washable Cover, web page www.amazon.com, available at least by Aug. 28, 2016.
Blephasteam Goggles for Dry Eye, web page www.amazon.co.uk, available at least by Aug. 28, 2016.
Eye Hydrating Mask with MediBeads, web page www.amazon.com, available at least by Oct. 22, 2016.
Japan Steam Heated Eye Mask, web page, available at least by Jun. 6, 2017.
Eye-Press Self Heating Warm Compress for the Eyes, web page www.riteaid.com, available at least by Aug. 28, 2016.
EyeGiene Insta-Warmth System for Dry Eyes, web page www.amazon.com, available at least by Aug. 28, 2016.
Wireless Eye Massager Machine with Heating and Bluetooth, web page www.amazon.com, available at least by Jun. 6, 2017.
Dry Eye Compress, EyeWarmers Brand, web page www.careandhome.com, available at least by Jun. 7, 2017.
Chronic Dry Eyes, web page www.firststreetonline.com, available at least by Jun. 6, 2017.
The Dry Eye Relief Kit, web page www.hammacher.com, available at least by Jun. 6, 2017.
ThermalOn Dry Eyes Moist Heat Compress, web page www.jet.com, available at least by Jun. 6, 2017.
TheraPearl Eye-ssential Mask, web page, available at least by Jun. 6, 2017.
Hot Gel Compress for Dry Eye Treatment, web page www.walmart.com, available at least by Jun. 6, 2017.
Dry Eye Compress with HydroHeat Machine Washable Cover, web page www.zabiva.com, available at least by Jun. 6, 2017.
Blackie, Caroline A., et al., Using warm compresses to treat meibomian gland disease, Optometry Times, Aug. 12, 2015.
C.A. Blackie OD PHD FAAO, et al, "Using warm compresses to treat meibomian gland disease", Optometry Times, Optometry, Dry eye, Aug. 12, 2015.
International Search Report and Written Opinion, PCT Application PCT/US2017/049100, dated Jan. 2, 2018.
Notice of Non-Final Rejection S. Korean Patent Application 10-2019-7008295, KIPO< dated Nov. 24, 2021.

* cited by examiner

EYE MASK

CROSS-REFERENCE TO RELATED APPLICATIONS

This application claims priority to U.S. provisional application 62/380,534, now U.S. Pat. No. 10,667,951 B2 filed on Aug. 29, 2016 and is entitled Eye Mask. The '534 provisional is incorporated by reference, in its entirety, into this application.

TECHNICAL FIELD

The present application relates to processes, devices, systems, and articles of manufacture involving eye masks. More particularly, the present application relates to processes, devices, systems, and articles of manufacture involving ophthalmic masks configured to provide therapeutic or other benefits to a wearer of the mask.

BACKGROUND

Sleep masks may be worn by a user to cover his or her eyes and promote a dampening of ocular stimulus for the wearer, i.e., serving as a blindfold. These masks may be worn during passenger travel and during sleep. Sleep masks often include both a headband portion and a mask portion where the headband serves to hold the mask portion over the eyes of the wearer.

BRIEF DESCRIPTION

Processes, devices, systems, and articles of manufacture involving ophthalmic masks are described herein. These processes, devices, systems, and articles of manufacture may involve eye masks configured to provide therapeutic or other benefits to a wearer of the mask. These benefits may derive from the placement and operation of a heat source of a mask embodiment as well as the use or application of a moisture supply configured to provide moisture from the mask to a wearer and/or to capture or trap moisture around the eye of a wearer and promote retention of that moisture. This moisture supply may be reusable and may be replenishable as well. Thus, the moisture supply may be washed or otherwise cleaned such that it may be reused over and over again for a prolonged period of time, e.g., days, weeks, months, or years. The moisture supply may also be replenishable such that when being reused over and over again, additional moisture may be applied to the moisture supply such that a wearer can receive the benefits of moisture therapy during repeated ongoing use of a mask. Similarly, the mask may also be configured such that moisture is trapped around the eye, and this moisture serves as a source or resupply of moisture to the wearer.

Thus, embodiments may provide various features including: providing sustained warming to the eye area of a user and providing specifically designed cleanable sheets, which may be removed and easily replaced and cleaned and may be reused. The heat, or cleanliness, or both properties, from the replaceable or reusable liners, e.g., sheets may serve to relieve or reduce stress of a user. Other benefits, including treating the thickening oils in eyelid glands, may also be realized through the application of embodiments.

Embodiments may include systems for providing heat and moisture to the eye region of a person. These systems may comprise a heating core configured with dual eye regions and a bridge connecting the dual eye regions. These dual eye regions may be symmetrical and spaced apart from each other with a bridge where the bridge may be configured to space the dual eye regions apart from one another. The dual eye regions may also be asymmetrical in order to provide different levels of treatment to the eye region of a wearer. Also, each eye region may be configured with a flap, the flap possibly secured to the heating core along one or more sides of the flap, where the flap may be configured to move outwardly and away from the eye region into an open position or with both sides having adjustable lengths to the strap and in other configurations as well. These systems may also include a head securement, where the head securement may be configured to at least two portions of the heating core. An electrical resistance heat source may also be included in embodiments, wherein the electrical resistance heat source may be positioned within each flap of the heating core. Still further, a cover sleeve may also be included in embodiments. This cover sleeve may be configured to slide on and off of one of the flaps with the cover sleeve having a first external water-resistant surface and a second external surface, the second external surface different than the first external water-resistant surface and that can have a mix of the same or similar water-resistant surface as for the external surface combined with a water-retaining fabric, centered over the person's eye. These one or more cover sleeves may be held in place with hook and loop fasteners and with other securement methodologies as well. In preferred embodiments the fastening methodologies can provide securement but may also provide for release and reconnection so the fabric may be treated, cleaned or otherwise administered.

Embodiments may also include an eye mask comprising a repositionable strap, a heating core, a power source, a controller, and one or more slip covers. The heating core may comprise at least one flap where the flap includes electrically resistant wiring and the heating core may be configured to be placed over one or both eyes of a person. Two flaps or multiple flaps may also be employed where each flap, some of the flaps, or most of the flaps contain resistant wiring or other heating mechanism.

A device for providing moisture as well as heat to Meibomian glands may also be provided in embodiments. This device may comprise a power source, an elastic headband, a heating core, and a single large liner, e.g., sleeve, as well as a plurality of liners, e.g., sleeves. The heating core may include a pair of flaps, and each of the flaps may contain a heating element configured to receive power from the power source. In embodiments, each of the cover sleeves of the pair of cover sleeves may be configured to surround a majority of one of the flaps of the pair of flaps of the heating core.

Numerous embodiments are possible beyond those specifically described above and below. The embodiments described here are illustrative and should not be considered to be limiting. This includes that processes described herein may be undertaken in various orders unless a specific order is called for in the applicable claim or description. Moreover, fewer or more features or actions may accompany those specifically described herein. Likewise, disclosed embodiments, whether in the brief summary or detailed description may be further modified, including being altered using features and processes selected from different embodiments and using features and processes in different orders and configurations.

There are various adaptations of embodiments, and many permutations may be employed within the spirit and scope of this disclosure. Those of skill will understand that the invention is not to be limited to only those embodiments described herein and that other embodiments and applications consistent with the teachings herein would also fall within the scope of this disclosure. For example, and as explained in more detail below, these other permutations can include variations in design of an ophthalmic mask, how the heating core or other heat source is preconfigured, the location and texture of cover sleeves, and the materials used to manufacture each of these components, as well as still other permutations.

DETAILED DESCRIPTION

Figure 1:
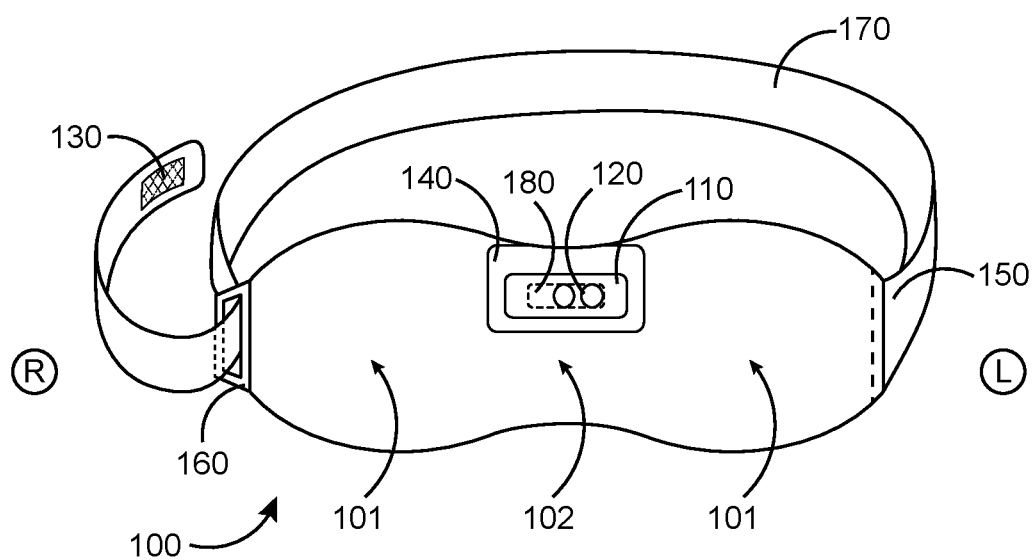
FIG. 1 shows a perspective front view of a heating core as may be employed in embodiments.

Embodiments may be employed for various purposes and have various configurations and features. Embodiments can include a mask to be positioned over the eyes and the glands of a user. The use of heat and moisture may provide therapeutic benefits, including treatment of Meibomian gland disease and other sources of dry eye, as well as physical benefits such as aiding in holding the eyes closed while sleeping and including promoting relaxation and reduction of stress. Masks may be worn by users in various locations including while at home, during airplane or other travel, at work, in controlled environments, and in other locations as well. When used, masks may assist in or serve to melt or otherwise treat thickened oils in the Meibomian glands, which are the glands that produce the oily layer of the tear film of the eyelids. Embodiments may be worn periodically, over short and longer periods of time, and may, for example, be used several times throughout the day as well as overnight, e.g., while the wearer is sleeping or otherwise in a dormant state. Start-up and configuration time, as well as effort needed to prepare a mask for use, may be aided through the use of sleeves as well as moisture supplies and the configuration of a heating core. Embodiments may be powered by various sources, including corded and cordless power sources. Preferred embodiments may have cordless power sources, such as battery power and inductive power supplies. Embodiments may have streamlined profiles and be preferably lighter in weight, e.g., weighing about 1, 2, 3, 4, 5, 6, 7, or 8 ounces. Embodiments may also have low profiles, which can promote accessibility and use, and may be helpful in other regards as well, including transport and storage. Lightweight polymers, carbon reinforced fabrics, and other light but resilient materials may be employed for the mask. The cover sleeve or sleeves may themselves be made from various materials including having different properties for different surfaces of the sleeve. For example, the inwardly facing portion of a sleeve, which will be near or in contact with an eyelid of a wearer, may be soft and include moisture retaining characteristics. And, the outwardly facing portion of a sleeve may have different characteristics including being opaque to light and perhaps being receptive to printing ink for decorative designs and/or receptive to embroidery for monogramming purposes.

As noted, embodiments, may be portable and readily taken on voyages for use in, for example, hotels or on transportation, such as planes or trains, in which preparing moist heated towels would present a challenge. The cover sleeves of embodiments, which may be reusable and replenishable, may serve to enhance sanitary conditions of the mask and to provide moisture/humidity directly to and in the area of the glands. In embodiments, these sleeves may also have drops of organic liquid with all-natural or synthetic aromas specifically formulated for safe use around the eyes added to them for an additional "aromatherapy"/stress-relieving effect.

Embodiments may include a core heating element made of a material that preferably would be thin, light-weight, and flexible (like fabric or resistant wiring, but preferably water-resistant and preferably resistant to melting/burning). As noted, these materials may include polymers, carbon fabrics, textiles, rubbers, wiring and combinations thereof. Other materials may also be used. Embodiments may be shaped generally like a typical light-blocking mask, similar to the fabric eye-masks seen on airlines, but may have resistant wiring woven or otherwise positioned throughout the area of the material or fabric with heating capabilities and may be connected to a preferably light-weight rechargeable battery which may be part of the mask and also may be resident in other devices. A possible variation may be a modified design in which the mask would be sectioned so that one eye can be heated while the other eye is uncovered, allowing the user to use the uncovered eye for visual tasks or in situations where one eye needs to be heated, but the other eye is not in a condition to be heated. In this modified design, the slip cover may be configured to be positioned over a single eye of the wearer and the heating core may be connected to the battery case and/or power controller or other source but not to the frame in such a way as to form two semi free-floating flaps on either side (to the right and left) of the battery casing or other power source. As described elsewhere, the slip cover may be comprised of various materials and fabrics, each having different or shared properties to provide various functionality for the clip cover and the eye mask. For example, the inwardly facing material may be a fabric with moisture holding capabilities while the outwardly facing material may be more durable or tough and may provide enhanced light blocking capabilities. Still other property differences may exist between the inwardly facing fabrics or other materials and the outwardly facing fabrics or other materials.

The placement of the battery casing/power source may also be located elsewhere on the heating core frame and the battery and its casing may be split up into two or more parts. Similarly, multiple battery cases and microprocessors may be employed in embodiments. These battery cases and microprocessors may be positioned on various locations of the eye mask, including the strap, the loop, and the heating core. The slip covers may preferably be of the same material compositions as the aforementioned ones, but may be smaller in size and shaped somewhat like pouches and may have fasteners, e.g., Velcro®, or a purse string or some other form of attachment on the open end to attach to the battery case and/or power controller and may have some form of fastener on the closed end to attach the pouch-enclosed heating element to an open frame that the battery case and/or power controller may be part of. Both flaps may be used simultaneously so that both eyes may be heated at the same time, or one or the other flap may be used alone, so that one side can be heated at a time. The fasteners on the flaps may serve to secure the moist heating elements to the frame so as to keep the elements secured against the eye or eyes being heated.

In embodiments, a flat low-profile manual switch may be located on the surface of a battery casing or elsewhere on the heating core and may be operated by a user, who may turn the battery or other power source on to generate heat in the material receiving electrical current from the power source. When a current source is employed, electricity through resistant wiring may serve to generate heat. Other sources of heat could include chemical reactions or fabrics with inherent heating capabilities (such as far-infrared generating fabric). In preferred embodiments, a microprocessor or other system manager may provide various operational modes described herein. These modes may include that maximum heat may be limited to 43.5 or 45 degrees Celsius or possibly another temperature in order to safely and effectively melt the oils in the Meibomian glands without damaging surrounding tissue. Electrical sources of heat may employ a circuit-breaker designed to limit the heat from reaching over 43.5 degrees Celsius or other target temperature and may have different or additional design criteria as well. In preferred embodiments, the elevated temperatures should be maintained for two to four to six to eight to fifteen to twenty to thirty minutes in order for the therapeutic heat to penetrate through the tarsal plate, fat, skin and vessels of the eyes ahead of reaching the Meibomian glands. There may be a cycling of heat being generated with short pauses of one to one-and-half to two minutes within a larger set time frame such as a total of fifteen to twenty minutes, with longer breaks in between, e.g. fifteen to twenty to thirty minutes before the cycle repeats itself. Regardless of the source of heat, there would preferably be included a mechanism to limit the heat production to a maximum target temperature.

In embodiments, a battery casing may be mounted onto and fit within a surface area of a firm heat-resistant lightweight plastic or carbon fiber mount. In embodiments, the battery casing may have approximate sizes of 2 cm H×4 cm L×the minimal thickness of plastic to promote not breaking while under its intended use. Preferably, the dimensions of the battery casing or casings may be modified such as to house the optimal battery size and shape to provide the maximum possible power to the power source while still keeping the profile of the unit as low and the weight as low as possible without losing integrity and function of the compress. Reduced weight of this battery casing or casings or other power source casing is also preferred in embodiments. A casing mount may be sewn into special "fabric" or other material of the mask to secure it in its place. And, in embodiments, the battery casing may have a profile that would extend from the surface of the plastic platform approximately 1 cm.

In embodiments, there may be a broad elastic "breathable" adjustable strap that may be sewn-in to "fabric" or other material of the mask on one side of the heating core with the other end of the strap going through a plastic loop sewn into the other side of the heating core "fabric" to then fasten to itself with hook and loop fasteners as well as other securement systems. Which side is fixed and which side has the adjustable fasteners can be switched or both sides can have plastic loops for straps to go through and secure to themselves as described. In embodiments, the length of this strap in conjunction with length of the mask may be designed to fit the typical range of adult human head circumferences. Various different sizes of the mask can also be made where these different sizes can include one for men and one for women/older children.

Embodiments may employ machine-washable and replaceable fabric covers/sleeves with some specially designed to add moisture to the heating process, as well as some designed to add a customizable element to the design. In embodiments, the outside of this cover sleeve may preferably be a flexible plastified water-resistant fabric or fabric that dries very rapidly, such as spandex, that may preferably have a selection of designs and colors to choose from and may also have a small rectangular hole on its surface designed to fit snuggly over the battery/switch unit to prevent shifting of the cover sleeve during use and to allow the user to access the switch. In embodiments, the inside (side towards or against the user) may include a moisture-bearing cloth that may preferably be lint-free or unlikely to produce lint and may have few if any volatile chemicals to preferably be considered "chemical-free" and as hypoallergenic as possible. In embodiments, the cloth may have the texture of a bath towel fabric, such as terry cloth. In embodiments moisture-bearing fabric may preferably stay wet less than 30 minutes to as long as an hour. In preferred embodiments, heat and moisture may be maintained for at a least period of twenty minutes, although other time periods, including 15, 25, 30, 35, 40, 45, 50, 60, 70, and 90 minutes may also be employed. Still further, the heat may be cycled on and off during the treatment. For example, heat may remain on during the first twenty minutes and then turn off for three minutes and then turn on for fifteen minutes. Other on-off cycle times, both uniform, and nonuniform, may be employed. Still further, different intensities of heat may also be employed, with lower temperatures being used during the first cycle time and then higher or different temperatures being used during subsequent on cycle times, or vice versa. And, temperatures may also be set to gradually increase or decrease during a cycle time. A microprocessor may be employed to control operation of the power source and the heating materials as well as other operations of components.

In use, the cover sleeves of embodiments may preferably be moistened by the user with tap water (warm temperature preferably), distilled water, or other moisture source and may then, preferably before turning the unit on, be slipped over the heating core from preferably one of the sides, although it may be slipped from the top and bottom as well. During use, the moistened side should preferably be against or otherwise facing the user's eyes.

In use, after slipping the moistened cover over the heating element of embodiments, the user may thread a flexible strap through a plastic loop located, preferably from the side of the mask preferably oriented such that a hook and loop fastener or other fastener system portion is on an exterior surface of the strap (i.e., away from the skin of the user) when fastened. In embodiments, users may take care to reduce the likelihood of the strap getting twisted to avoid discomfort during use. In embodiments, a user may initially place the mask over his or her eyes with the strap loosened and then proceed to tighten the strap around his or her head to his or her level of comfort. In embodiments, the mask should preferably be secured to the head of a user firmly enough to prevent excessive shifting of the mask during use. The strap may be secured with hook and loop fasteners in embodiments. Other fastener systems, such as snaps and ties, may also be used. In embodiments, preferably after positioning the mask around the head, a user may move the switch on the outside of the mask to turn it on and activate the heat production. Once the user is done with using the mask, he/she can manually turn the switch off and remove the mask, or vice versa. In embodiments, the cover sleeve may be placed in the laundry to be washed or may be washed by hand before its next use.

As noted above, in embodiments, drops of organic, natural or synthetic, concentrated scents may be added to the mask or the cover sleeve or both. The scents may also be pre-imbibed in a flat thin material inserted between the cover sleeve and the mask. These scents may preferably be made safe for use on the eyes for aromatherapy and may also be derived to combat eyelash mites, i.e., Demodex. In preferred embodiments, drops may be placed on the moist side of the cover sleeve after wetting the sleeve for use and before placing the mask over the eyes.

FIG. 1 shows a perspective front view of a heating core as may be employed in embodiments. Labelled in FIG. 1 are the heating core 100, the mounting plate 140, power case 110, microprocessor 180, sliding switch 120, strap 170, strap end 150, loop 160, and hook/rough fasteners 130. The loop 160 may be made from various materials including plastic, cloth, metal, and carbon fiber reinforced matrixes. Likewise, the mounting plate 140, power case 110, and sliding switch 170 may be made from various materials including plastic, cloth, metal, and carbon fiber reinforced matrixes. The strap end 150 may be secured to the heating core 100 with stitches, hook and loop fasteners, and other securement means. The strap 170 itself may be made from elastic fiber or other material configured to allow for easy and comfortable securement of the heating core to the head of a wearer. The combination of the strap or other securement means and the heating core 100 may be considered a mask as recited in this application. As can be seen, the hook fasteners 130 are positioned to allow the strap 170 to be loosened or tightened in order to secure the heating core 100 and strap 170 to the head of a user with adjustable degrees of tightness. In use, a wearer may open the hook fasteners 130 adjust the strap 170 and heating core, and resecure the hook fasteners 130 to provide for a comfortable fit.

Figure 2:
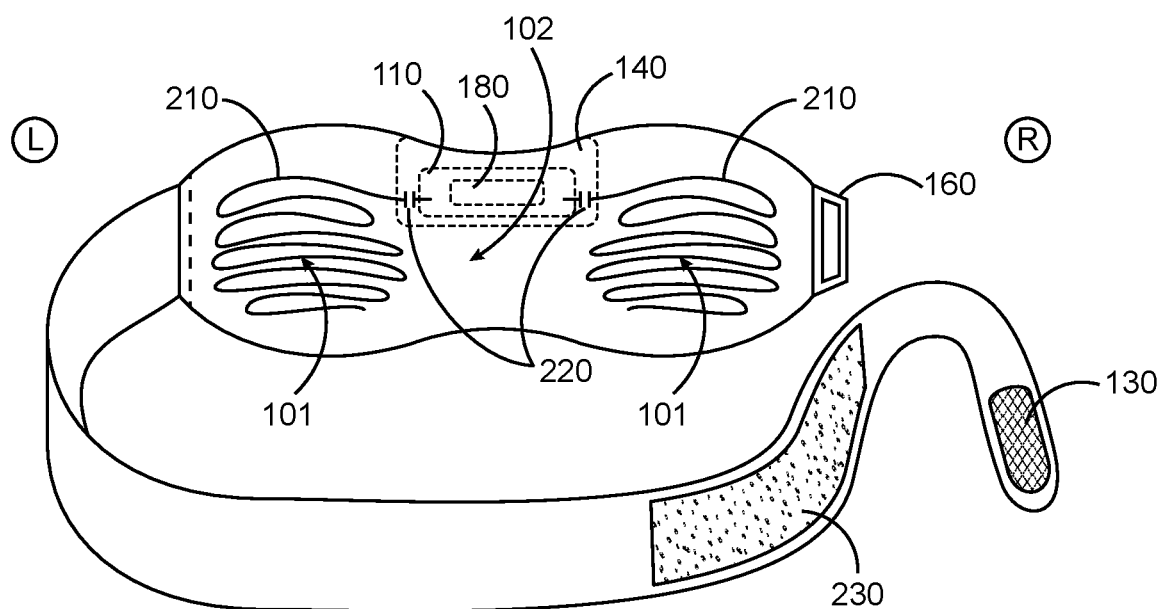
FIG. 2 shows a perspective back view of the heating core of FIG. 1 as may be employed in embodiments.

FIG. 2 shows a perspective back view of the heating core of FIG. 1 as may be employed in embodiments. Labelled in FIG. 2 are the electrically resistant wiring 210, circuit breakers 220, microprocessor 180, loop/soft fasteners 230, hook/rough fasteners 130, loop 160, mounting plate 140, power case 110, eye region 101, and bridge 102. As can be seen, the electrically resistant wiring 210 is positioned to reside over the eyes of a wearer. Powered by the batteries or other power source in the battery case and/or power controller 110, the wiring 210 preferably will generate the heat described above in order for the warmth to reach the eyes, glands, etc. of the wearer. The power source, which is shown as a battery case and/or power controller here, may be managed such that the wiring 210 of the heating core 100 is controlled to generate heat as described herein. The loop 160 of FIG. 2 shows how the end of the strap 170 may pass through and be used to secure the heating core to the face of a wearer.

Figure 3:
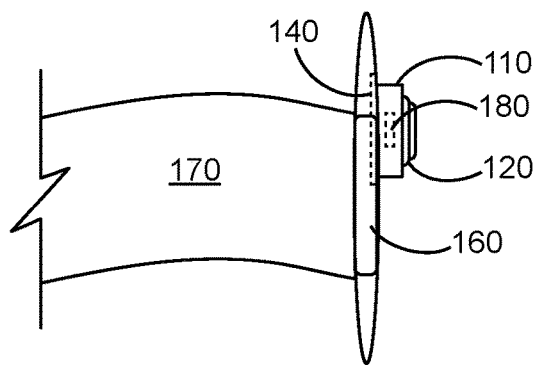
FIG. 3 shows a right-side view of the heating core of FIG. 1 as may be employed in embodiments.

FIG. 3 shows a right-side view of the heating core of FIG. 1 as may be employed in embodiments. Labelled in FIG. 3 are the loop 160, the sliding switch 120, microprocessor 180, the power case 110, strap 170 and the mounting plate 140. This upright orientation of the heating core shows how a mask may be positioned when worn by a sitting wearer.

Figure 4:
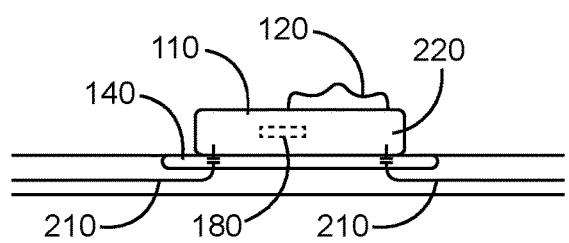
FIG. 4 shows a top downward view of the heating core of FIG. 2 as may be employed in embodiments.

FIG. 4 shows a top downward view of the heating core of FIG. 2 as may be employed in embodiments. The circuit breakers 220 are shown in this view along with the sliding switch 120, the power case 110, microprocessor 180, the mounting plate 140, and the wiring 210. This top down view shows how the switch on the face of the heating core may be readily moved by a wearer. This view also shows how the circuitry of the breakers 220 may be positioned in relation to the mounting plate 140. Having the wiring pass thought the plate in this fashion may serve to support the wiring 210 as well as serve to retard any unwanted stray voltages that have passed through the breakers to reach the wearer.

Figure 5:
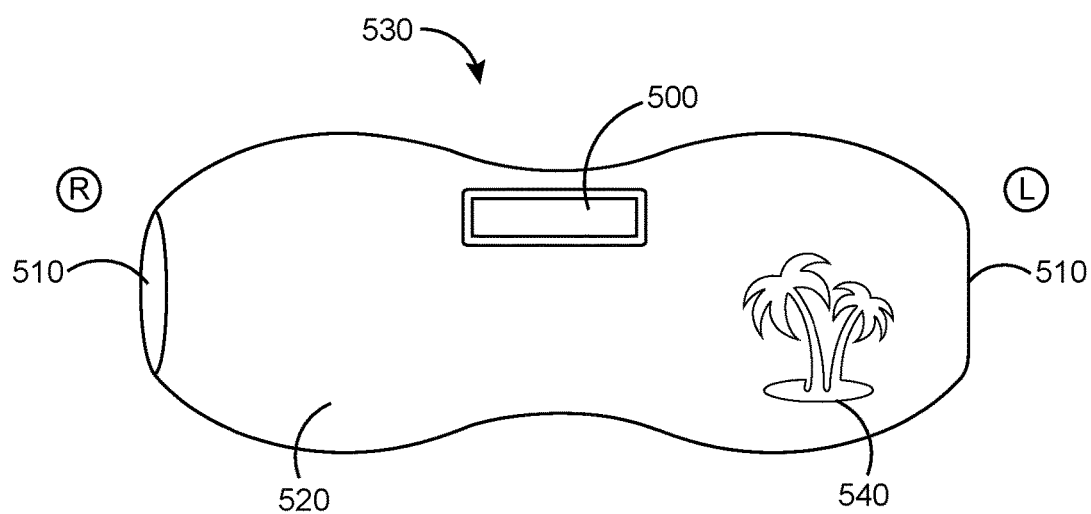
FIG. 5 shows a front-perspective view of a cover sleeve as may be employed in embodiments.

FIG. 5 shows a front-perspective view of a cover sleeve as may be employed in embodiments. The cover sleeve 530 is shown with an opening 500 to allow access to the switch of the heating core shown and described above. Also shown in FIG. 5 is that the sleeve 530 has open ends 510, a printed icon 540, and water resistant decorated plastified, or otherwise fast-drying and/or water-resistant, fabric 520. This sleeve 530 is shaped and configured to fit around and over the heating core shown and described above.

Figure 6:
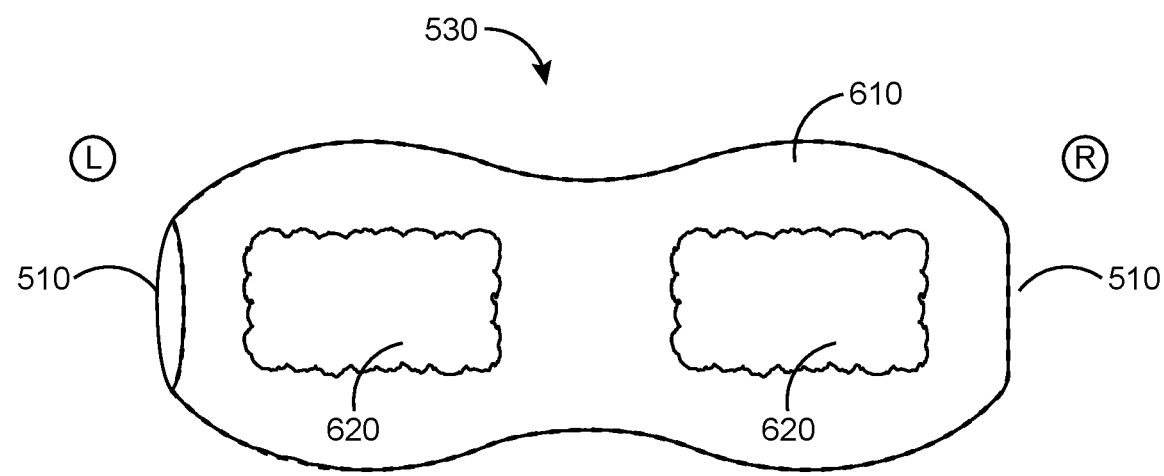
FIG. 6 shows a back-perspective view of the cover sleeve as may be employed in embodiments.

FIG. 6 shows a back-perspective view of the cover sleeve 530 as may be employed in embodiments. Labelled in FIG. 6 are the open ends 510 and the fabric 610 which may be a combination of fabrics that may include a base of fabric of similar or same material as fabric 520 with a different fabric 620 that is absorbent and is attached, preferably sewn onto fabric 520. This fabric 620 is preferably lint free, or low-lint, and as free of volatile chemicals (e.g., "chemical-free") as possible. The fabric 620 is also preferably absorbent so as to retain moisture in a suitable manner. Fabric 620 may preferably be bath towel like. The fabric 620 may be positioned primarily over the eyes of a wearer. Thus, the cover sleeve 530 may have two different outer surfaces, 520 and 610, with each outer surface having different properties and performing different tasks.

Figure 7:
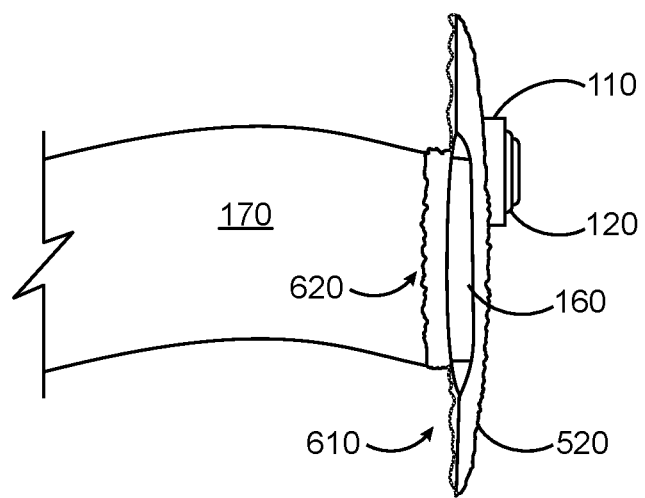
FIG. 7 shows a side view of a cover sleeve as in FIG. 5 installed over a heating core as in FIG. 1 as may be employed in embodiments.

FIG. 7 shows a side view of a cover sleeve as in FIG. 5 installed over a heating core as in FIG. 1 as may be employed in embodiments. As can be seen, the fabric 520 is facing away from the wearer and the fabric 610 is facing towards the wearer. Also labelled in FIG. 7 are the strap 170, the sliding switch 120, the power case 110, and the loop 160. The opening 500 of the sleeve 530 allows the switch 120 to be readily accessible even though the cover sleeve 530 is positioned around the heating core 100.

Figure 8:
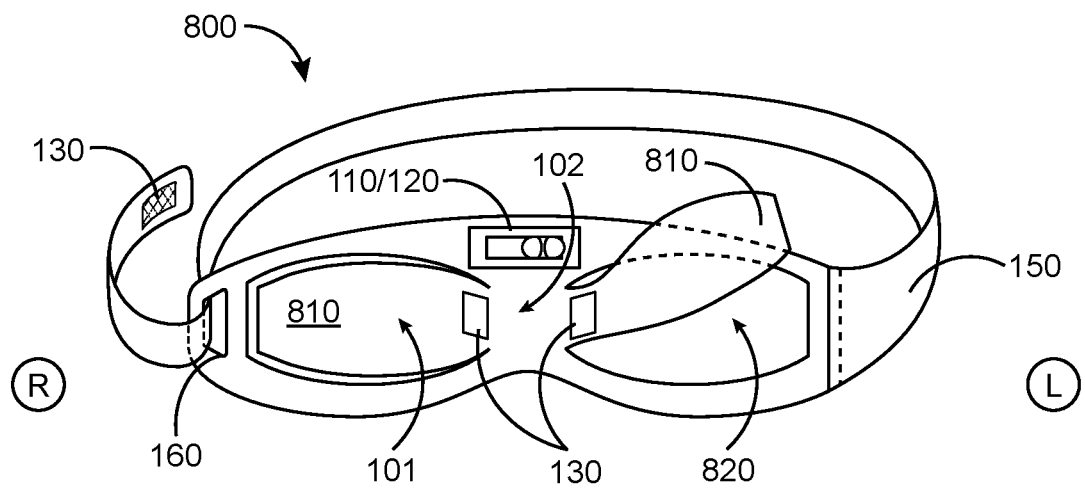
FIG. 8 shows a perspective front view of a heating core as may be employed in embodiments.

FIG. 8 shows a perspective front view of a heating core and strap as may be employed in embodiments. The flaps 810 are labelled in FIG. 8 along with hook/rough fasteners 130, strap end 150, loop 160, and power case/switch 110/120. The flaps may be secured along one edge, as shown in FIG. 8. This edge may be any of the edges around the internal opening 820 of the heating core 800. Also labeled is eye region 101.

Figure 9:
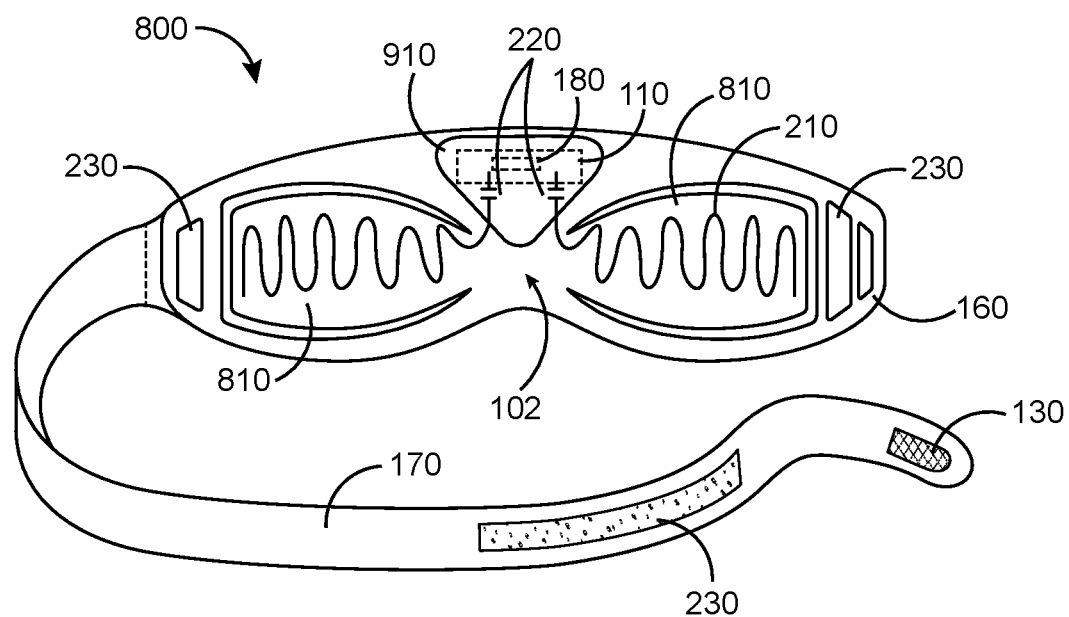
FIG. 9 shows a perspective back view of the heating core of FIG. 8 as may be employed in embodiments.

FIG. 9 shows a perspective back view of the heating core 800 and strap 170 of FIG. 8 as may be employed in embodiments. Also labelled in FIG. 9 are the mounting plate 910 which may include a water-resistant cushion 1210, the power case 110, microprocessor 180, the electrical wiring 210, the loop/soft fasteners 230, the loop 160, the flaps 810, circuit breakers 220, and hook/rough fasteners 130.

Figure 10:
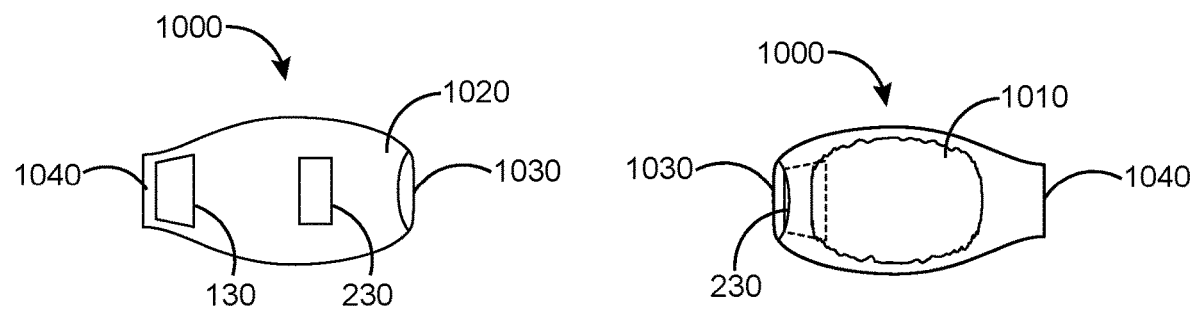
FIG. 10 shows a pair of cover sleeves as may be employed in embodiments.

FIG. 10 shows a pair of cover sleeves 1000 as may be employed in embodiments. Also labelled in FIG. 10 are hook/rough fasteners 130, loop/soft fasteners 230, water retaining fabric 1010, fast-drying or water-resistant fabric 1020, closed ends 1040, and open ends 1030.

Figure 11:
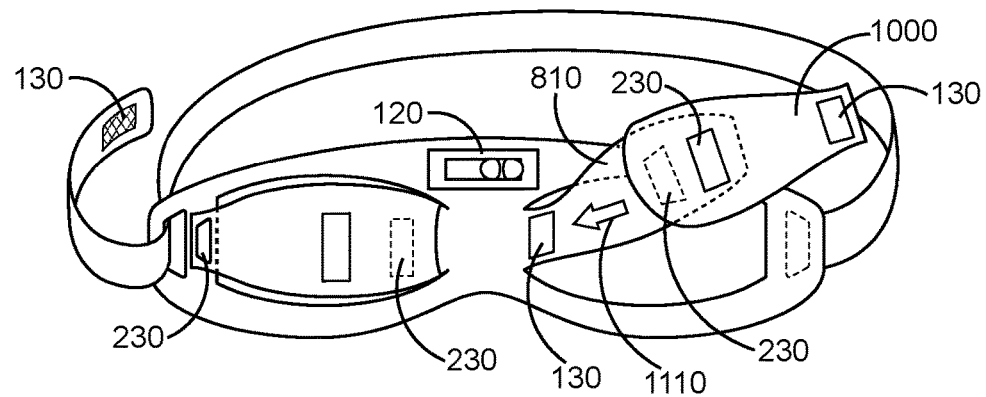
FIG. 11 shows the pair of cover sleeves partially and fully positioned over flaps of the heating core of FIG. 8 as may be employed in embodiments.

FIG. 11 shows the pair of cover sleeves 1000 partially and fully positioned over flaps 810 of the heating core of FIG. 8 as may be employed in embodiments. Also labelled in FIG. 11 are hook/rough fasteners 130, loop/soft fasteners 230, switch 120, and sleeves 1000. Arrow 1110 shows how the sleeve 1000 may be slid onto the flap 810. Also labeled is sliding switch 120.

Figure 12:
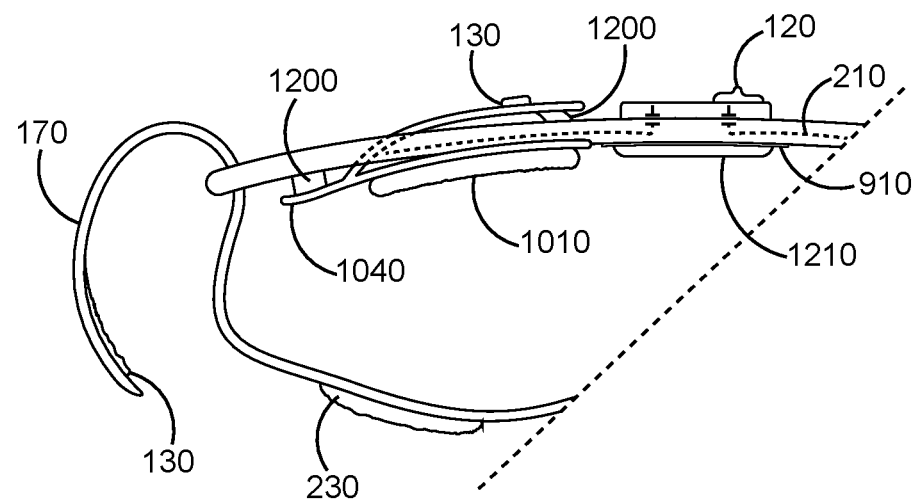
FIG. 12 shows a partial plan view of a mated cover sleeve and a flap of the heating core of FIG. 8 as may be employed in embodiments.

FIG. 12 shows a partial plan view of a mated cover sleeve 1000 and a flap 810 of the heating core of FIG. 8 as may be employed in embodiments. Labelled in FIG. 12 are strap 170, loop fasteners 130, closed ends 1040, water retaining fabric 1010, secured hook/rough and loop/soft fasteners 1200, loop hook/rough fastener 130, loop/soft fastener 230, switch 120, wiring 210, water proof cushion 1210 and mounting plate 910.

Figure 13:
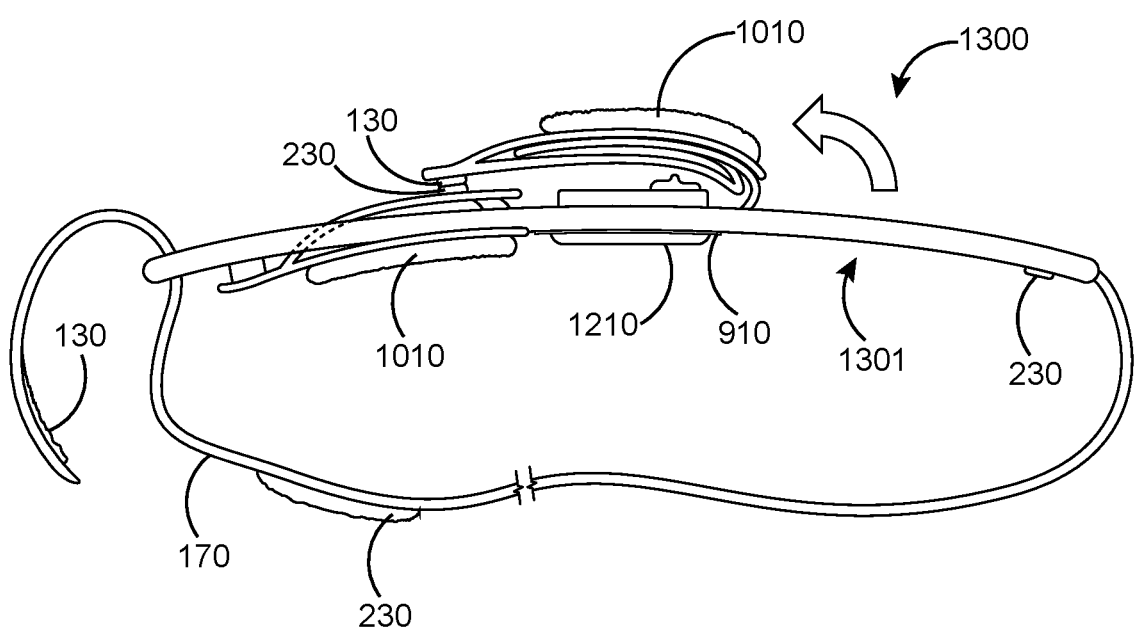
FIG. 13 shows a plan view of cover sleeves mated with each flap of the heating core of FIG. 8 as may be employed in embodiments.

FIG. 13 shows a plan view of cover sleeves mated with each flap of the heating core of FIG. 8 as may be employed in embodiments. Labelled in FIG. 13 are hook/rough fasteners 130, moisture retaining fabric 1010, strap 170, loop/soft fasteners 230, opening 1301, flap movement arrow 1300, and mounting plate 910, and water proof cushion 2010.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" and/or "comprising," when used in this specification, specific the presence of stated features, integers, steps, operations, elements, and/or components, but do not preclude the presence or addition of one or more other features, integers, steps, operation, elements, components, and/or groups thereof.

It should be noted that a use of the terms "first", "second", and "third", and the like may be used herein to modify elements performing similar and/or analogous functions. These modifiers do not imply a spatial, sequential, or hierarchical order to the modified elements unless specifically stated.

The description of the embodiments of the present invention has been presented for purposes of illustration and description, but is not intended to be exhaustive or limited to the invention in the form disclosed. Many modifications and variations will be apparent to those of ordinary skill without departing from the scope and spirit of the invention. The embodiments were chosen and described in order to best explain the principles of the invention and the practical application, and to enable others of ordinary skill in the art to understand the invention for embodiments with various modifications as are suited to the particular use contemplated.

What is claimed is:

1. An eye mask comprising:
   a strap;
   a heating core comprising a first flap where the first flap comprises electrically resistant wiring;
   a power source, the power source connected to the electrically resistant wiring;
   a controller that, when in use, regulates power from the power source to the electrically resistant wiring; and
   a first cover sleeve, the first cover sleeve sized and shaped to surround at least a majority of the first flap,
   wherein the first flap is at least partially detached from the heating core, so that the first flap can be positioned either against or away from an eye of a user independently of the heating core.

2. The eye mask of claim 1 wherein the heating core comprises a second flap, the second flap mimicking the shape of the first flap, wherein the second flap is at least partially detached from the heating core, such that the second flap can be secured in a position either against or away from an eye of the user independently of the first flap and independently of the heating core.

3. The eye mask of claim 2 wherein each of the first and second flaps are secured along a perimeter edge of each flap to the heating core.

4. The eye mask of claim 1 wherein the power source comprises a battery, a rechargeable battery, an inductive power supply, or a combination thereof.

5. The eye mask of claim 1, (a) wherein the heating core comprises a second flap, the second flap mimicking the shape of the first flap, and (b) wherein the first cover sleeve is sized and shaped to surround at least a majority of the first flap and at least a majority of the second flap, and the eye mask comprises a second cover sleeve sized and shaped to surround at least a majority of the second flap.

6. The eye mask of claim 5, wherein the eye mask comprises a second cover sleeve, and the second cover sleeve and the second flap are detachable and reattachable to each other.

7. The eye mask of claim 5, wherein the eye mask comprises a second cover sleeve, and the second cover sleeve comprises two external surfaces, the first external surface comprising a surface comprising cloth or other fabric, and the second external surface different from the first external surface.

8. The eye mask of claim 5, wherein the first cover sleeve is sized and shaped to surround at least a majority of the first flap and at least a majority of the second flap.

9. The eye mask of claim 8, wherein the first cover sleeve is independently detachable and reattachable to the first flap and to the second flap.

10. The eye mask of claim 5, wherein the first cover sleeve is sized and shaped to surround at least a majority of the first flap and at least a majority of the second flap, and the second cover sleeve comprises two external surfaces, the first external surface comprising a surface comprising cloth or other fabric, and the second external surface different from the first external surface.

11. The eye mask of claim 1 wherein the first cover sleeve and the first flap are detachable and reattachable to each other.

12. The eye mask of claim 1, wherein the first cover sleeve comprises two external surfaces, the first external surface comprising a surface comprising cloth or other fabric, and the second external surface different from the first external surface.

13. A treatment device comprising:
a power source;
a strap;
a heating core; and
a first cover sleeve,
wherein the heating core comprises a first flap and a second flap, each of the flaps containing a heating element, wherein, when in use, the heating elements receive power from the power source, the power source coupled to the strap or to the heating core,
wherein the first cover sleeve is sized and shaped to surround at least a majority of at least the first flap of the pair of flaps of the heating core,
wherein the first and second flaps of the heating core are attached to the heating core along one edge, so that one flap may be positioned against one eyelid of a user while the other flap may be positioned away from the other eyelid of the user independently of each other and independently of the heating core.

14. The treatment device of claim 13 wherein the first cover sleeve has two external surfaces, the first external surface comprising a first material and the second external surface comprising a second material, the first material and the second material being different from one another.

15. The treatment device of claim 14, wherein the second external surface of the first cover sleeve comprises a terry-cloth knap, an other moisture-retaining material, or both.

16. The treatment device of claim 13 wherein the first cover sleeve is sized and shaped to surround a majority of each of the first and second flaps of the heating core.

17. The treatment device of claim 13, further comprising a second cover sleeve that is sized and shaped to surround at least a majority of the second flap.

18. A system for providing heat, moisture, or both to the eye region of a person, the system comprising:
a power source; and
a heating core;
wherein the heating core comprises a pair of flaps, each of the flaps containing a heating element, wherein, when in use, the heating elements receive power from the power source,
wherein each flap of the pair of flaps is at least partially detached from the heating core, so that each flap can be positioned against an eyelid of a user independently of the other flap and independently of the heating core, and
so that one flap may be positioned against a first eyelid of a user, while the other flap may be not positioned against a second eyelid of the user.

19. The system of claim 18, further comprising: a first detachable cover sleeve, wherein the first detachable cover sleeve is sized and shaped to surround a majority of at least a first flap of the pair of flaps of the heating core.

20. The system of claim 19, wherein the first detachable cover sleeve comprises two external surfaces, the first external surface comprising a surface comprising cloth or other fabric, and the second external surface different from the first external surface.

21. The system of claim 18, further comprising: a first detachable cover sleeve, wherein the first detachable cover sleeve is shaped and sized to surround a majority of each of the first flap and a second flap of the pair of flaps of the heating core.

22. The system of claim 21, wherein the first detachable cover sleeve comprises two external surfaces, the first external surface comprising a surface comprising cloth or other fabric, and the second external surface different from the first external surface.

23. The system of claim 18, wherein the power source comprises a battery, a rechargeable battery, an inductive power supply, or a combination thereof.

* * * * *